United States Patent

Lahrmann et al.

Patent Number: 6,035,471
Date of Patent: Mar. 14, 2000

[54] METHOD FOR DETECTING IMPERMISSIBLY HIGH SCALING IN A WATER-CONDUCTING DOMESTIC APPLIANCE

[75] Inventors: Andreas Lahrmann; Lothar Knopp, both of Berlin, Germany

[73] Assignee: BSH Bosch und Siemens Hausgeraete GmbH, Munich, Germany

[21] Appl. No.: 09/084,714

[22] Filed: May 26, 1998

[30] Foreign Application Priority Data

May 26, 1997 [DE] Germany .......................... 197 21 976

[51] Int. Cl.[7] .................................................. D06F 33/02
[52] U.S. Cl. ................................................ 8/158; 68/12.02
[58] Field of Search ............................... 68/12.02, 12.04, 68/12.05, 12.07, 12.12, 12.19, 12.21, 12.27, 13 R; 134/113; 8/156, 159

[56] References Cited

U.S. PATENT DOCUMENTS

| | | | |
|---|---|---|---|
| 5,048,139 | 9/1991 | Matsumi et al. | 68/12.02 |
| 5,134,867 | 8/1992 | Kiuchi | 68/12.02 |
| 5,438,507 | 8/1995 | Kim et al. | 8/158 |
| 5,589,935 | 12/1996 | Biard | 68/12.02 |
| 5,800,628 | 9/1998 | Erickson et al. | 68/12.02 |

FOREIGN PATENT DOCUMENTS

| | | | |
|---|---|---|---|
| 54-144044 | 11/1979 | Japan . | |
| 61-125390 | 6/1986 | Japan . | |
| 61-232895 | 10/1986 | Japan | 68/12.02 |
| 3-114499 | 5/1991 | Japan | 68/12.02 |

*Primary Examiner*—Frankie L. Stinson
*Attorney, Agent, or Firm*—Herbert L. Lerner; Laurence A. Greenberg

[57] ABSTRACT

Impermissibly high scaling is ascertained of an optical measurement section in which the turbidity of a washing liquid is detected in a domestic appliance that is operated with hard water, such as a washing machine or dishwasher. The appliance has an evaluation circuit for the measured signals from the measurement section and a microprocessor for binding the measurement results into the sequence control system of the appliance. The system is suitable for indicating impermissibly high scaling and for taking into account attenuation of the measurement section by chalk deposits during the determination of the turbidity of the washing liquid. Before or during the initial commissioning of the appliance, a threshold value for the permissible attenuation of the measurement section by future chalk deposits is stored, during each working cycle of the appliance, the attenuation of the measurement section is measured during a cycle section which is carried out without clouded washing liquid, whereby the attenuation is transformed into a measured value and compared with the threshold value, and the microprocessor outputs a control signal for the sequence control system when the measured value has reached or approximately reached the threshold value.

6 Claims, 1 Drawing Sheet

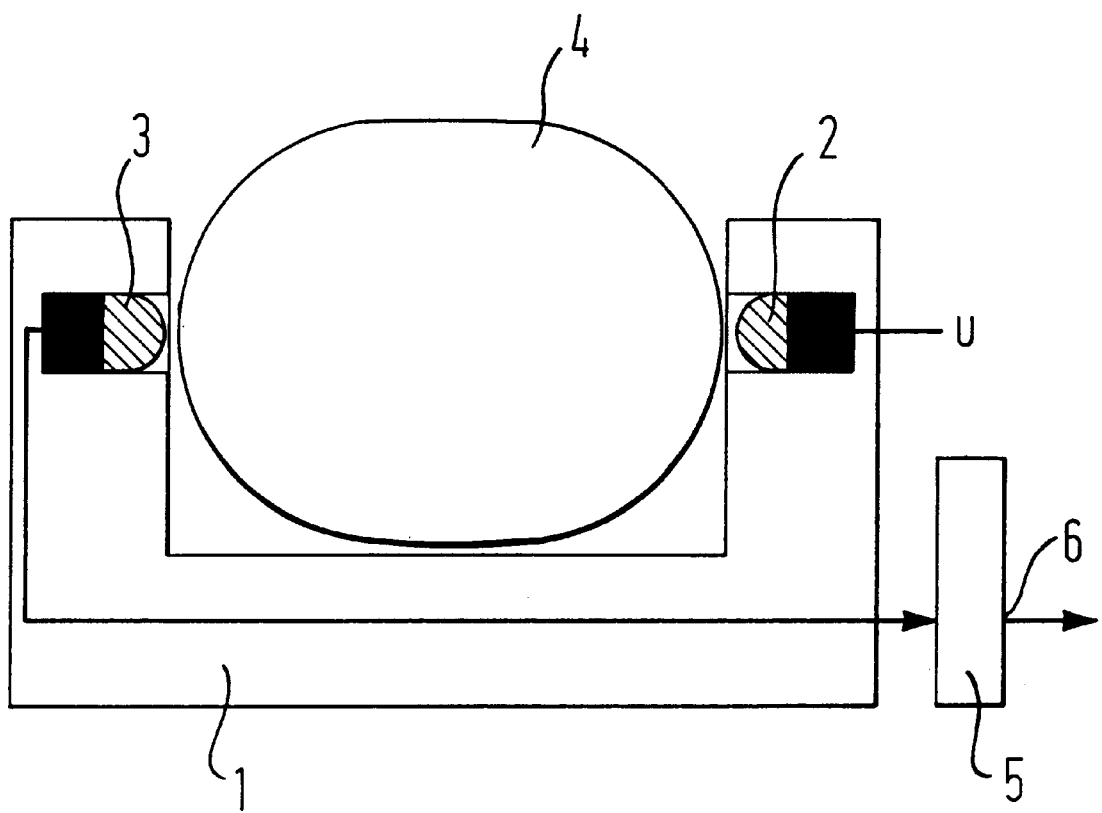

METHOD FOR DETECTING IMPERMISSIBLY HIGH SCALING IN A WATER-CONDUCTING DOMESTIC APPLIANCE

BACKGROUND OF THE INVENTION

1. Field of the Invention

The invention relates to a method for detecting impermissibly high scaling of an optical measurement section for measuring the turbidity of a washing liquid in a domestic appliance that is operated with hard water, such as a washing machine or dishwasher. The appliance has an evaluation circuit for the measured signals from the measurement section and a microprocessor for converting the measurement results into the sequence control system of the appliance.

In the case of appliances to which hard water is supplied, such as washing machines or dishwashers, there is the problem that the service life of the appliance or else the performance of the appliance may be adversely affected as a result of chalk deposits. It is often not possible for such chalk deposits to be detected by the user of the appliance, or the degree to which these deposits are damaging cannot be assessed by the user.

German published, non-prosecuted application 195 21 326 A1 (corresponding U.S. application Ser. No. 08/877,101; commonly owned) discloses a method for calibrating turbidity measured values, in which the measured values are calibrated as a function of variable temperatures. However, that process does not take another variable influence, namely the risk of scaling of the optical measurement section, into consideration. Since this measurement section dries out again after each working process—this is because, for reasons not explained specifically here, it is best located far above the level of the amount of residual water that remains after the washing liquid has been pumped out of the container of the machine—it is possible for residual water droplets to leave chalky edges behind when they dry out, and these gradually grow to form a dense covering. At first, slight chalk deposits are barely disruptive. However, when a covering that is also visible to the naked eye has been produced, then, even in the case of clear water, the measurement beam in the optical measurement section will already be attenuated to such an extent that the signal evaluation circuit will detect a supposed washing-liquid turbidity which depends on the thickness of the covering.

SUMMARY OF THE INVENTION

It is accordingly an object of the invention to provide a TITLE, which overcomes the above-mentioned disadvantages of the heretofore-known devices and methods of this general type and which, on the one hand, is suitable for indicating impermissibly high scaling and, on the other hand, also takes into account the attenuation of the measurement section by chalk deposits during the determination of the turbidity.

With the foregoing and other objects in view there is provided, in accordance with the invention, a method for detecting impermissibly high scaling of an optical measurement section measuring a turbidity of a washing liquid in a domestic appliance, wherein the domestic appliance has an evaluation circuit receiving measured signals from the measurement section and a microprocessor for including the measurement results into a sequence control of the appliance, the method which comprises:

before or during an initial commissioning of a domestic appliance, storing a threshold value for a permissible attenuation of a measurement section by future chalk deposits; and during each working cycle of the domestic appliance and during a cycle which is carried out without clouded washing liquid, measuring a current attenuation of the measurement section;

transforming the current attenuation into a measured value and comparing the attenuation with the threshold value; and outputting a control signal with a microprocessor for the sequence control when the measured value has substantially reached the threshold value.

The threshold value stored in the microprocessor may be prescribed in accordance with a permissible amount of chalk deposit. The user of the appliance is thus given an indication well before a damaging level of chalk deposits is reached, so that the user can initiate descaling measures in a specific manner.

With the second of the above-noted objects of the invention in view, there is provided a method which comprises the following step:

before or during initial commissioning of a domestic appliance, ascertaining a starting value for an attenuation of an unloaded measurement section and storing the starting value with a microprocessor;

during each new working cycle of the domestic appliance, forming a correction value from a difference between a respective measured value and the starting value, and storing the correction value with the microprocessor; and weighting the measured value with the correction value and feeding the changed value to the sequence control system as a turbidity value.

The two solutions may advantageously be combined with each other. In that case, the turbidity measurements become very reliable as a result of the continuously updated correction, until the degree of scaling that is recognized as damaging is reached.

In accordance with an added feature of the invention, the microprocessor forms an average of the measured signals received during a predetermined number of working cycles of the domestic appliance, and the average is compared with the threshold value. This makes it possible to avoid the situation where an indication is given as a result of brief signal fluctuations which are not based on correspondingly severe scaling.

In accordance with an additional feature of the invention, the control signal triggers an indicating element of the domestic appliance.

In accordance with another feature of the invention, after the measured signals from the measurement section have exceeded the threshold value a number of times, the threshold value is increased. Hence, although the appliance can continue to be operated, the attention of the user is continually drawn to the high degree of scaling.

In accordance with a concomitant feature of the invention, the subsequently ascertained turbidity values are weighted (corrected) with the stored correction value. The influence of chalk deposits on the turbidity measurement of the washing liquid can be eliminated in that the turbidity values that are measured while the washing-liquid turbidity is subsequently being ascertained are corrected as a function of the stored correction value.

Other features which are considered as characteristic for the invention are set forth in the appended claims.

Although the invention is illustrated and described herein as embodied in a method for detecting impermissibly high scaling in a water-conducting domestic appliance, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

The sole FIGURE of the drawing is a schematic view of a measurement section and a water-conducting pipe.

DESCRIPTION OF THE PREFERRED EMBODIMENTS

Referring now to the figure of the drawing in detail there is seen a measurement section 1 that is used in the inventive method. The measurement section 1 has a light transmitter 2 and a light receiver 3, which are disposed opposite each other on the outer circumference of a pipe section 4. The pipe section is formed of transparent material. The light transmitter 2 is fed from a voltage source U. The output from the light receiver 3 constitutes the output from the measurement section 1 and is connected to an associated input of a microprocessor 5. A control signal that depends on the output signal from the measurement section 1 appears at the output 6 of the microprocessor 5. By means of this control signal, a non-illustrated indicating device on the domestic appliance may be activated.

As the chalk deposit on the pipe section 1 increases, the light radiated by the light transmitter 2 is attenuated, with the result that the magnitude of the output signal from the light receiver 3 changes in a corresponding manner. The magnitude of the output signal from the light receiver 3 is compared with a threshold value that is stored in the microprocessor 5. If the magnitude of the output signal from the light receiver 3 reaches the magnitude of this threshold value, the microprocessor 5 outputs a control signal at its output 6, and this control signal activates an indicating element of the domestic appliance.

Since the pipe section 4 receives the water fed to the appliance or discharged from the appliance, chalk is deposited on the pipe section 4 in the same way as in the appliance itself. This chalk deposit would disrupt the satisfactory measurement of the washing-liquid turbidity resulting from detergent or dirt constituents, with the result that the measurement results would be falsified, and incorrect or untimely effects on the process would be derived from them. During such a determination of the turbidity of the washing liquid, it is possible to compensate for incorrect measurements, as a result of chalk deposits having occurred in the meantime on the pipe section 4, by the measured turbidity values being corrected using correction values that are stored in the microprocessor 5. Such correction values are ascertained during each new working cycle of the appliance, and constitute a measure of the scaling reached at any one time on the pipe section 4.

On the other hand, however, such chalk deposits on the pipe section 4 are also a measure of corresponding chalk deposits in the appliance, so that the level of deposits in the appliance is also registered by measuring the chalk deposits on the pipe section 4. The indicating device that is activated as a function of the scaling of the pipe section 4 thus signals to the user of the appliance that the scaling of the appliance has reached a value which has an unfavorable influence on the performance of the appliance or of its components and/or on its service life.

In this way, on the one hand the attention of the user is drawn to the damage to the appliance that is threatened by scaling. On the other hand, such an indication can also aid the specific use of descaling agents and, as a result, excessive use of the latter can be avoided.

We claim:

1. A method for detecting impermissibly high scaling of an optical measurement section measuring a turbidity of a washing liquid in a domestic appliance, wherein the domestic appliance has an evaluation circuit receiving measured signals from the measurement section and a microprocessor for including the measurement results into a sequence control of the appliance, the method which comprises:

before or during an initial commissioning of a domestic appliance, storing a threshold value for a permissible attenuation of a measurement section by future chalk deposits; and during each working cycle of the domestic appliance and during a cycle which is carried out without clouded washing liquid, measuring a current attenuation of the measurement section;

transforming the current attenuation into a measured value and comparing the attenuation with the threshold value; and outputting a control signal with a microprocessor for the sequence control when the measured value has substantially reached the threshold value.

2. The method according to claim 1, which comprises forming, with the microprocessor, an average of the measured signals received during a predetermined number of working cycles of the domestic appliance, and comparing the average with the threshold value.

3. The method according to claim 1, which comprises activating an indicating element of the domestic appliance with the control signal.

4. The method according to claim 1, which further comprises, after the measured signals from the measurement section have exceeded the threshold value a number of times, increasing the threshold value.

5. A method for detecting impermissibly high scaling of an optical measurement section measuring a turbidity of a washing liquid in a domestic appliance, wherein the domestic appliance has an evaluation circuit receiving measured signals from the measurement section and a microprocessor for including the measurement results into a sequence control of the appliance, the method which comprises:

before or during initial commissioning of a domestic appliance, ascertaining a starting value for an attenuation of an unloaded measurement section and storing the starting value with a microprocessor;

during each new working cycle of the domestic appliance, forming a correction value from a difference between a respective measured value and the starting value, and storing the correction value with the microprocessor; and weighting the measured value with the correction value and feeding the changed value to the sequence control system as a turbidity value.

6. The method according to claim 5, which comprises weighting the subsequently ascertained turbidity values with the stored correction value.

* * * * *